(12) United States Patent
Okimura et al.

(10) Patent No.: US 9,737,634 B2
(45) Date of Patent: Aug. 22, 2017

(54) NON-WOVEN FABRIC CONTAINING BONE PROSTHETIC MATERIAL

(75) Inventors: Yusuke Okimura, Takatsuki (JP); Kazuyoshi Kita, Takatsuki (JP); Naoyuki Hanaki, Takatsuki (JP); Yasunori Nemoto, Takatsuki (JP)

(73) Assignee: SUNSTAR INC., Osaka (JP)

( * ) Notice: Subject to any disclaimer, the term of this patent is extended or adjusted under 35 U.S.C. 154(b) by 0 days.

(21) Appl. No.: 14/001,559

(22) PCT Filed: Feb. 28, 2012

(86) PCT No.: PCT/JP2012/054965
§ 371 (c)(1),
(2), (4) Date: Aug. 26, 2013

(87) PCT Pub. No.: WO2012/118090
PCT Pub. Date: Sep. 7, 2012

(65) Prior Publication Data
US 2013/0338790 A1  Dec. 19, 2013

(30) Foreign Application Priority Data

Feb. 28, 2011 (JP) ................. 2011-042450

(51) Int. Cl.
*A61L 27/36* (2006.01)
*A61L 27/46* (2006.01)
*A61F 2/28* (2006.01)

(52) U.S. Cl.
CPC .......... *A61L 27/36* (2013.01); *A61F 2/28* (2013.01); *A61L 27/46* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 2009/0028921 A1* | 1/2009 | Arinzeh | 424/423 |
| 2009/0148489 A1* | 6/2009 | Cooper | A61L 27/446 424/423 |
| 2009/0246259 A1 | 10/2009 | Kita et al. | |
| 2009/0324673 A1 | 12/2009 | Yao et al. | |
| 2010/0172952 A1* | 7/2010 | Srouji et al. | 424/423 |

FOREIGN PATENT DOCUMENTS

| | | |
|---|---|---|
| CN | 101128226 | 2/2008 |
| CN | 101406711 | 4/2009 |
| GB | 2 259 252 | 3/1993 |
| JP | 2000-262608 | 9/2000 |
| JP | 2003-210569 | 7/2003 |
| JP | 2007-325543 | 12/2007 |
| WO | 2006/056740 | 6/2006 |
| WO | 2007/063820 | 6/2007 |
| WO | 2007/132186 | 11/2007 |
| WO | 2007/148682 | 12/2007 |

OTHER PUBLICATIONS

Gupta, D., et al., "Nanostructured biocomposite substrates by electrospinning and electrospraying for the mineralization of osteoblasts," Biomaterials 30: 2085-2094 (2009).*
Haaparanta, A.-M., et al., Journal of Tissue Engineering and Regenerative Medicine 4: 366-373 (2010).*
Jang, J.-H., et al., "Electrospun materials as potentital platforms for bone tissue engineering," Advanced Drug Delivery Reviews 61: 1065-1083 (2009).*
International Search Report issued Mar. 27, 2012 in International (PCT) Application No. PCT/JP2012/054965.
K. Fujihara et al., "Guided Bone Regeneration Membrane made of Polycaprolactone/Calcium Carbonate Composite Nano-Fibers", Biomaterials, vol. 26, pp. 4139-4147, 2005.
Supplementary Extended European Search Report dated Jul. 28, 2015 for related European Patent Application No. 12752347.0.
Hae-Won Kim et al., "Electrospinning biomedical nanocomposite fibers of hydroxyapaite/poly(lactic acid) for bone regeneration", Journal of Biomedical Materials Research Part A, 2006, vol. 79A, No. 3, pp. 643-649.
Japanese Office Action dated Feb. 7, 2017, issued in corresponding Japanese Patent Application No. 2013-171529. (with English translation).
Damien Le Nihouannen et al., "Micro-architecture of calcium phosphate granules and fibrin glue composites for bone tissue engineering", Biomaterials, vol. 27, No. 13, 2005, pp. 2716-2722.

* cited by examiner

*Primary Examiner* — David J Blanchard
*Assistant Examiner* — Daniel F Coughlin
(74) *Attorney, Agent, or Firm* — Wenderoth, Lind & Ponack, L.L.P.

(57) ABSTRACT

An object of the present invention is to provide a bone regeneration material suitable for bone (in particular, alveolar bone) regeneration. The present invention provides a non-woven fabric containing a bone prosthetic material wherein the bone prosthetic material is included between biocompatible fibers that constitute the non-woven fabric. The non-woven fabric may be suitably used as a bone regeneration material (in particular, a dental bone regeneration material).

8 Claims, 11 Drawing Sheets

Fig. 4
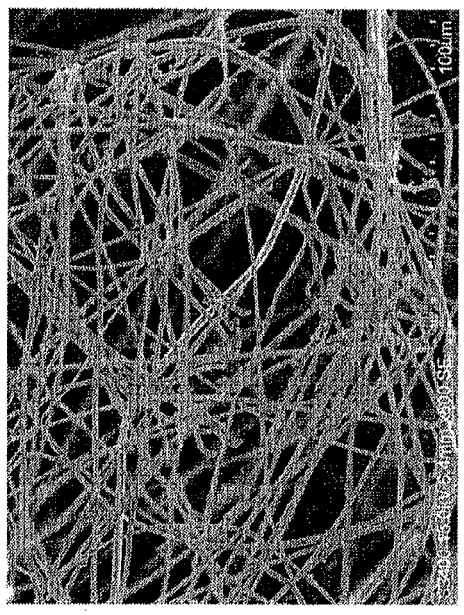
Electron-microscopic image of non-woven fabric portion ×500
Electron-microscopic image 75x
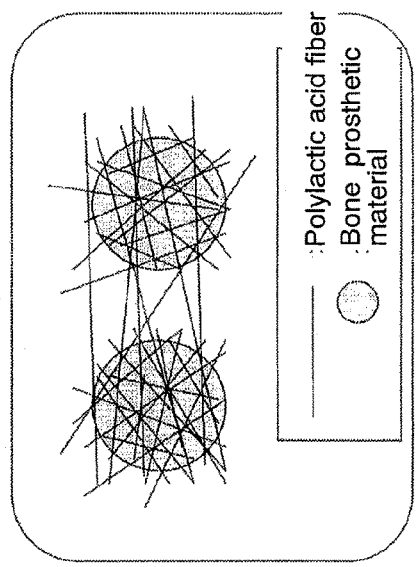
Schematic diagram
: Polylactic acid fiber
: Bone prosthetic material

- - - denotes the outline of the implant, and .... denotes the border between the tissue penetrating the implant and the region not penetrated

- - - denotes the outline of the implant, and .... denotes the border between the tissue penetrating the implant and the region not penetrated

Fig. 7

| Non-woven fabric | Porosity of Non-woven fabric (%) | Porosity of fibers of Non-woven fabric (%) | Cross sectional view (piece of HE stained tissue) "<" denotes the uppermost surface of non-woven fabric | Maximum Cell infiltration distance |
|---|---|---|---|---|
| Non woven fabric A without bone prosthetic material | 78.3 | 78.3 | 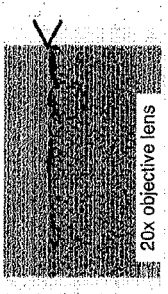 20x objective lens | 41 μm |
| Three-dimensional non-woven fabric B | 83.5 | 91.7 |  20x objective lens | 146 μm |
| Three-dimensional non-woven fabric C | 92.5 | 98.6 |  20x objective lens | 376 μm |
| Three-dimensional non-woven fabric D | 94.8 | 99.2 |  10x objective lens | 580 μm |

Fig. 8
| | Pore size (μm) | Cell infiltration (piece of HE stained tissue) (images corresponding to 2 portions of each fabric) | (Evaluation) |
|---|---|---|---|
| Three-dimensional non-woven fabric β | 8.8 | 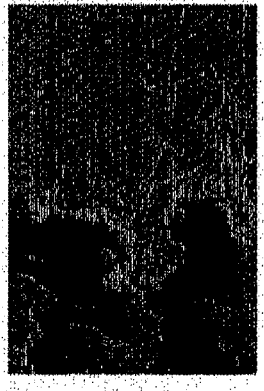 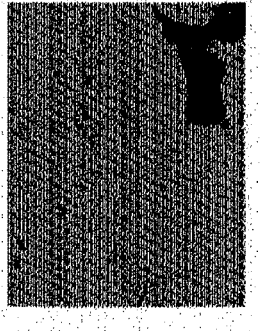 | Good |
| Three-dimensional non-woven fabric γ | 16.0 | 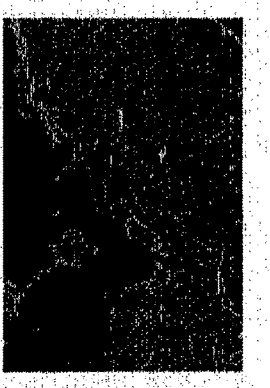  | Superior |

Fig. 10

| | Non-woven fabric (i) | Non-woven fabric (ii) | Non-woven fabric (iii) |
|---|---|---|---|
| Cell infiltration (piece of HE-stained tissue) the white arrow denotes the cell infiltration distance from the non-woven fabric surface; — denotes 150μm | 40x lens | 20x lens | 20x lens |
| (Evaluation) | Unsatisfactory | Good | superior |
| Maximum infiltration distance | 11.5 μm | 143.7 μm | 317.0 μm |
| Pore size | 2.8 μm | 11.4 μm | 14.7 μm |

NON-WOVEN FABRIC CONTAINING BONE PROSTHETIC MATERIAL

TECHNICAL FIELD

The present invention relates to a non-woven fabric containing a bone prosthetic material.

BACKGROUND ART

Nowadays, "implant treatments" are universally prevalent. Implant treatments designate procedures for repairing tooth loss due to aging, periodontal diseases, or the like, by implanting an artificial tooth root into an alveolar bone, and covering the implanted tooth root with an artificial crown and an superstructure.

When a tooth is lost, (i.e., when a tooth comes out), the alveolar bone that has supported the tooth is immediately absorbed and reduced. Therefore, during implant treatments, alveolar bone is often found to be of insufficient thickness for the implantation of artificial tooth root. The insufficient thickness of the alveolar bone will likely make the implanted artificial tooth root unstable. Therefore, when the alveolar bone has an insufficient thickness, bone grafting or bone regeneration is conducted.

The GBR (guided bone regeneration) method is one of the common techniques for alveolar bone regeneration. In the GBR method, pulverized autogenous bone or a bone prosthetic material is placed in the part (affected part) where the alveolar bone is reduced, and a membrane (also called a shield membrane or a GBR membrane) is placed thereon (i.e., the affected part filled with the bone prosthetic material is covered with the membrane. In this manner, the GBR method promotes regeneration of alveolar bone while preventing entry of the gingival tissue. However, the existing bone prosthetic materials are insufficient in cell attachment and cell proliferation. For this reason, alveolar bone regeneration takes a long time. Moreover, since the existing bone prosthetic materials have insufficient adhesiveness to alveolar bones and insufficient retention in the affected part, leakage of the material often occurs even after the material is covered with the GBR membrane.

Further, although implant treatments occasionally use bone cement, bone cement has a drawback in that it blocks cell infiltration.

As described above, currently available bone regeneration materials suffer from insufficient cell attachment and cell proliferation.

In order to solve such drawbacks, study and development was continued to invent a bone regeneration material suitable for bone (in particular, alveolar bone) regeneration (e.g., see Patent Documents 1 and 2).

CITATION LIST

[Patent Document 1] WO2007/132186
[Patent Document 2] JP2007-325543A

SUMMARY OF INVENTION

Technical Problem

An object of the present invention is to provide a bone regeneration material suitable for bone (in particular, alveolar bone) regeneration.

Solution to Problem

Surprisingly, the inventors of the present invention found that a non-woven fabric containing a bone prosthetic material wherein the bone prosthetic material is included between the fibers, which are biocompatible fibers, can serve as a bone regeneration material that ensures significantly high cell (in particular, osteoblast) proliferation efficiency (high cell proliferation ability). The inventors conducted attempts to further improve this non-woven fabric, and finally completed the present invention.

Specifically, the present invention encompasses the inventions of the following items.

[Item 1]
A non-woven fabric containing a bone prosthetic material wherein the bone prosthetic material is included between biocompatible fibers that constitute the non-woven fabric.

[Item 2]
The non-woven fabric according to Item 1, wherein the biocompatible fibers contain a biocompatible polymer.

[Item 3]
The non-woven fabric according to Item 2, wherein the biocompatible polymer is at least one member selected from the group consisting of polylactic acid, polyglycolic acid, polylactic acid-polyglycolic acid copolymer, polycaprolactone, chitin, collagen, polylysine, polyarginine, hyaluronic acid, sericin, cellulose, dextran, and pullulan.

[Item 4]
The non-woven fabric according to any one of Items 1 to 3, wherein the bone prosthetic material is at least one member selected from the group consisting of β-TCP (R-tricalcium phosphate), α-TCP (α-tricalcium phosphate), HA (hydroxyapatite), DCPD (dibasic calcium phosphate dihydrate), OCP (octacalcium phosphate), 4CP (tetracalcium phosphate), alumina, zirconia, calcium aluminate ($CaO$—$Al_2O_3$), aluminosilicate ($Na_2O$—$Al_2O_3$—$SiO_2$), bioactive glass, quartz, and calcium carbonate.

[Item 5]
The non-woven fabric according to any one of Items 1 to 4, wherein the bone prosthetic material has a particle diameter of about 50 to 5000 μm.

[Item 6]
The non-woven fabric according to any one of Items 1 to 5, wherein the non-woven fabric has a porosity of 78.5 to 97%.

[Item 7]
The non-woven fabric according to any one of Items 1 to 6, wherein the fibers of the non-woven fabric have a porosity of 80 to 99.99%.

[Item 8]
The non-woven fabric according to any one of Items 1 to 7, wherein the bulk density ($g/cm^3$) of the non-woven fabric is 0.1 to 0.6.

[Item 9]
A bone regeneration material comprising the non-woven fabric according to any one of Items 1 to 8.

[Item 10]
An osteoblast culture scaffold material comprising the non-woven fabric according to any one of Items 1 to 8.

[Item A-1]
A bone regeneration method comprising the step of applying the non-woven fabric according to any one of Items 1 to 8 to a target site of bone regeneration.

[Item A-2]
The bone regeneration method according to Item A-1, wherein the bone is alveolar bone.

[Item B-1]
The non-woven fabric according to any one of Items 1 to 8 for use in the treatment for bone regeneration.

[Item B-2]

The non-woven fabric according to Item B-1, wherein the bone is alveolar bone.

[Item C-1]

Use of the non-woven fabric according to any one of Items 1 to 8 for the manufacture of a bone regeneration formulation.

[Item C-2]

The use according to Item C-1, wherein the bone regeneration formulation is an alveolar bone regeneration formulation.

[Item C-3]

Use of the non-woven fabric according to any one of Items 1 to 8 as a cell scaffold in vitro.

Advantageous Effects of Invention

When the non-woven fabric containing a bone prosthetic material of the present invention is used as a cell culture scaffold, the cell (in particular, osteoblast) proliferation efficiency is significantly increased (that is, the cell proliferation ability is increased). Further, in particular, when the non-woven fabric is used as a scaffold for the culture of osteoblast, it provides the effect of an increase in bone regeneration efficiency, since the non-woven fabric contains a bone prosthetic material. Therefore, the non-woven fabric can be suitably used as a bone regeneration material. More specifically, in cases of bone damage due to external factors (for example, accident), or in cases of absorption or loss of bone due to internal factors (for example, osteoporosis, periodontitis, etc.), the non-woven fabric of the present invention enables quick bone regeneration (specifically, by being inplanted into or attached to the affected part).

BRIEF DESCRIPTION OF DRAWINGS

FIG. 4 Images (taken by a scanning electron microscope) of cross-sections of the non-woven fabric of the present invention.

FIG. 7 Images of HE-stained cells after performing cell cultures using different types of non-woven fabric as a scaffold; and cell infiltration distances found from the images.

FIG. 8 Results of pore size measurement of the non-woven fabrics; and images of HE-stained cells after performing cell cultures using the non-woven fabrics as a scaffold.

FIG. 10 Results of pore size measurement of the non-woven fabrics; images of HE-stained cells after performing cell cultures using the non-woven fabrics as a scaffold; and cell infiltration distances found from the images.

BEST MODE FOR CARRYING OUT THE INVENTION

Figure 1:
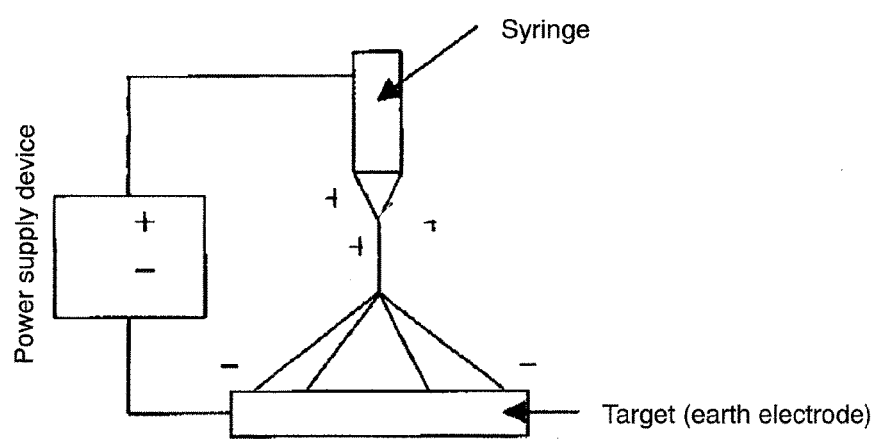
FIG. 1 A simple schematic view showing a non-woven fabric production process using an electrospinning method.

The present invention is more specifically described below. The term "mass" in this specification is equivalent to "weight."

The present invention relates to a non-woven fabric containing a bone prosthetic material. In the non-woven fabric, the bone prosthetic material is included between fibers that constitute the non-woven fabric. Further, these fibers are biocompatible fibers.

The bone prosthetic material contained in the non-woven fabric may be selected from known materials, including β-TCP (β-tricalcium phosphate), α-TCP (α-tricalcium phosphate), HA (hydroxyapatite), DCPD (dibasic calcium phosphate dihydrate), OCP (octacalcium phosphate), 4CP (tetracalcium phosphate), alumina, zirconia, calcium aluminate ($CaO$—$Al_2O_3$), aluminosilicate ($Na_2O$—$Al_2O_3$—$SiO_2$), bioactive glass, quartz, and calcium carbonate. More specifically, fragments containing these components (preferably, fragments of these components) may be used. The bone prosthetic material may be made of one of these components, or a combination of two or more components. The bone prosthetic materials made of a combination of two or more components include materials made of a fragment or fragments, each of which contains two or more components; or materials made of multiple fragments, each of which has a single component.

Further, each fragment of the bone prosthetic material has a size embeddable in a non-woven fabric or smaller. Each fragment may have an arbitrary form, such as a particle, a block shape, a cylindrical shape, and the like.

The particle diameter of each fragment of the bone prosthetic material is preferably less than the thickness of the non-woven fabric. More preferably, the particle size is about 50 to 5000 µm, further preferably about 75 to 5000 µm, further more preferably about 150 to 3000 µm, particularly preferably about 500 to 1500 µm. This particle diameter is a value found by a dry sieving method. More specifically, the particle size is a value found by using a RO_TAP (rotating and tapping) shaker containing a JIS Z8801 sieve. A bone prosthetic material having the specific particle diameter can be obtained through a dry sieving method. Further, the particle diameter of a bone prosthetic material with unknown particle diameter may also be found by a dry sieving method. The expression "particle diameter" herein is not to specify that the bone prosthetic material is limited to a powdered form, but only to define the above size range. The value of "particle diameter" defined herein can also be found for a bone prosthetic material having other shapes (for example, a block shape, a cylindrical shape, or the like).

The non-woven fabric of the present invention may also be selected from commercially available bone prosthetic materials. Examples thereof include OSFERION (Olympus Terumo Biomaterials Corp.), BONECERAM (Olympus Terumo Biomaterials Corp.), NEOBONE (MMT Co., Ltd.), Osteograft-S (Japan Medical Materials), and APACERAM (Pentax Corporation).

In the non-woven fabric of the present invention, the bone prosthetic material exists between multiple (a large number of) fibers of the non-woven fabric. More specifically, the bone prosthetic material is not incorporated within a single fiber, but incorporated between the fibers that constitute the non-woven fabric. In other words, the fibers of the non-woven fabric are present with the bone prosthetic material tangled therebetween. The fibers of the non-woven fabric of the present invention are biocompatible fibers containing a biocompatible polymer. The biocompatible fibers are preferably biodegradable in a living organism. The amount of the biocompatible polymer contained in the fibers is generally more than 50 mass %, preferably not less than 75 mass %, more preferably not less than 80 mass %, further preferably not less than 85 mass %, further more preferably not less than 90 mass %, particularly preferably not less than 95 mass %, most preferably substantially 100% (that is, a biocompatible fiber made only of a biocompatible polymer is most preferable).

A biocompatible polymer designates a polymer that causes little or no foreign body response when adhered to or embedded into a living tissue (in other words, a polymer that causes no adverse effect or severe stimulation in a living organism for a long period of time; i.e., it can coexist with living tissues while ensuring the original function). Examples of such biocompatible polymers include bioresorbable polymers and biodegradable polymers.

Specific examples of biocompatible polymers include polylactic acid, polyglycolic acid, polylactic acid-polyglycolic acid copolymer, polycaprolactone, polybutylene succinate, polyethylene succinate, polystyrene, polycarbonate, polyhexamethylene carbonate, polyarylate, polyvinylisocyanate, polybutyl isocyanate, polymethylmethacrylate, polyethylmethacrylate, poly-n-propylmethacrylate, poly-n-butyl methacrylate, polymethylacrylate, polyethylacrylate, polybutylacrylate, polyacrylonitrile, polyvinylacetate, polyvinylmethyl ether, polyvinylethylether, polyvinyl-n-propylether, polyvinylisopropylether, polyvinyl-n-butyl ether, polyvinylisobutyl ether, polyvinyl tertiary butyl ether, polyvinylchloride, polyvinylidenechloride, poly(N-vinylpyrrolidone), poly(N-vinylcarbazole), poly(4-vinylpyridine), polyvinylmethyl ketone, polymethyl isopropenyl ketone, polyethylene oxide, polypropylene oxide, polycyclopenteneoxide, polystyrene sulfone, Teflon® (polytetrafluoroethylene), polycyanoacrylate, polyether ether ketone, polyurethane, polyimide, polyvinyl chloride, polyethylene (including super-high molecular weight polyethylene), polypropylene, polyethylene terephthalate, polyvinylidene fluoride (polyvinylidene difluoride), polysulfone, polyether sulfone; and copolymers thereof and like synthetic polymers, regenerated cellulose, cellulose diacetate, cellulose triacetate, methylcellulose, propylcellulose, benzylcellulose, fibroin, natural rubber and like biomacromolecules and derivatives thereof. Examples also include chitin, gelatin, collagen, polyamino acid (polylysine, polyarginine), hyaluronic acid, sericin, dextran, and pullulan.

Among them, preferable biocompatible polymers include aliphatic polyesters such as polylactic acid, polyglycolic acid, polylactic acid-polyglycolic acid copolymer, polyhydroxybutyrate, polycaprolactone, polyethylene adipate, polybutylene adipate, polybutylene succinate, polyethylene succinate and polycyanoacrylate, or copolymers thereof; and aliphatic polycarbonates such as polybutylene carbonate or polyethylene carbonate. Further preferable examples include polylactic acid, polyglycolic acid, polylactic acid-polyglycolic acid copolymer, and polycaprolactone. Among them, polylactic acid is particularly preferable. These biocompatible polymers may be used solely, or in a combination of two or more.

Insofar as the effects of the present invention are not impaired, other polymers or compounds (for example, polymer copolymers, polymer blends, phospholipids, other compounds, and mixtures thereof) may be used.

The average fiber diameter of the fibers of the non-woven fabric is preferably about 0.05 to 20 µm, more preferably about 0.1 to 5 µm, further preferably about 0.1 to 3 µm. This range of average fiber diameter enables easy adhesion of osteoblast, and also is advantageous in terms of improving bone regeneration efficiency. The average fiber diameter is a value found by measuring the diameter of each fiber in an electron-microscopic image of the non-woven fabric, and finding an average diameter of 50 randomly selected fibers.

A suitable thickness of the non-woven fabric may be determined according to the affected part (the bone defect site to which the non-woven fabric is applied). The thickness is preferably about 0.1 to 5 cm, more preferably about 0.1 to 1 cm, further preferably about 0.1 to 0.5 cm. The "thickness" of the non-woven fabric herein designates a length of the non-woven fabric in the thickness-wise direction measured without applying pressure. The thickness can be measured using a thickness gauge (digital thickness gauge, Ozaki Co., Ltd., DG-205M), and the like.

The bulk density ($(g/cm^3)$), i.e., {non-woven fabric weight (g)/non-woven fabric bulk ($cm^3$)}) of the non-woven fabric of the present invention is preferably about 0.1 to 0.6, more preferably about 0.1 to 0.5, further preferably about 0.1 to 0.4, further more preferably about 0.1 to 0.3, yet more preferably about 0.15 to 0.25, particularly preferably about 0.15 to 0.2. If the bone prosthetic material contained in the non-woven fabric is β-TCP or α-TCP, it is particularly preferable that the bulk density falls within the above range. The bulk ($cm^3$) of the non-woven fabric here is found by cutting the non-woven fabric into a rectangle (about 4 $cm^2$), measuring the vertical length, the horizontal length, and the thickness of the rectangle using a thickness gauge; and multiplying the vertical length, the horizontal length, and the thickness.

The porosity of the non-woven fabric of the present invention is preferably about 78.5 to 97%; and more preferably about 80 to 97%, about 85 to 97%, about 90 to 97%, about 90 to 95%, about 91 to 95%, about 91.5 to 95%, and about 92 to 95%, in this order. The porosity (%) can be found from the density (true density) of the fibers of the non-woven fabric and the density of the bone prosthetic material. More specifically, the bulks of the fibers and the bone prosthetic material can be found by dividing the weight of the fibers contained in a 1 $cm^3$ portion of the non-woven fabric of the present invention and the weight of the bone prosthetic material by their true densities. Accordingly, by subtracting the total value of the bulks from 1 ($cm^3$) and multiplying the resulting value by 100, the porosity (%) of the non-woven fabric can be found. The following formula shows this calculation.

porosity of non-woven fabric (%)=[1−{(fiber weight/fiber true density)+(bone prosthetic material weight/bone prosthetic material true density)}]×100     [Math. 1]

The porosity (%) of the fiber portion of the non-woven fabric can also be found by dividing the bulk (cm³) of the fibers by a value obtained by subtracting the bulk (cm³) of the bone prosthetic material from 1 (cm³), and multiplying the calculation result by 100. The following formula shows this calculation.

porosity of fibers of non-woven fabric (%)=[1−[(fiber weight/fiber true density)/{1−(bone prosthetic material weight/bone prosthetic material true density)}]]×100   [Math. 2]

The porosity of the fibers of the non-woven fabric is preferably about 85 to 99.99%, more preferably about 90 to 99.99%, even more preferably about 97.5 to 99.99%, further preferably about 98 to 99.8%.

The true density in the present specification is found according to the constant volume expansion method. The measurement of true density can be performed, for example, using a dry automatic pycnometer (ACCUPYC 1330; Shimadzu Corporation).

The porosity of the non-woven fabric and the porosity of the fibers of the non-woven fabric that fall within the above range particularly facilitate cell infiltration; and also improve permeability of body fluid and blood, and enables easy invasion of new blood vessel upon tissue regeneration. In the present invention, the porosity of the fibers of the non-woven fabric of the present invention is higher than that of a general non-woven fabric. Although a restrictive interpretation is not desired, it is assumed that incorporation of a bone prosthetic material between fibers increases the porosity. Despite the high porosity between the fibers, when a pressure is applied on the non-woven fabric of the present invention, the thickness of the non-woven fabric is recovered to some extent by releasing the pressure (for example, when the non-woven fabric is pressed by a hand, the thickness will be recovered to some extent by removing the hand). This is also assumed to derive from the incorporation of a bone prosthetic material between the fibers.

The pore size of the non-woven fabric of the present invention is preferably about 0.5 to 500 μm, more preferably about 1 to 100 μm, further preferably about 2 to 50 μm, furthermore preferably about 3 to 30 μm, particularly preferably about 6 to 20 μm.

The pore size of the non-woven fabric in this specification designates the mode value of a measurement sample obtained by peeling off the surface layer of the non-woven fabric of the present invention. The mode value is found according to the half-dry method (ASTME1294-89) using a perfluoro polyester (class interval=1 μm). The measurement of pore size may be performed using a capillary flow porometer (CFP-1200-AEL, Porous Materials, Inc.).

Further, the non-woven fabric of the present invention has a coarse fiber portion and a dense fiber portion (more specifically, the fiber distribution has variable density). The interfiber distance of the dense fiber portion is preferably about 5 to 40 μm, more preferably about 10 to 30 μm, further preferably about 15 to 25 μm. The interfiber distance of the coarse fiber portion is preferably about 50 to 100 μm. The interfiber distance of the non-woven fabric in this specification designates a value found by detecting fibers from an image of a frozen block of non-woven fabric obtained by a microscope, and finding the distance using the detected fiber data according to the centroid method.

The proportion of the bone prosthetic material in the non-woven fabric of the present invention is preferably about 10 to 98%, more preferably about 50 to 98%, further preferably about 80 to 98%.

The proportion of the bone prosthetic material in this specification designates a value found by the following formula.

{bone prosthetic material contained in non-woven fabric (g)/non-woven fabric (g)}×100(%)

The amount (g) of the bone prosthetic material in the non-woven fabric is found by measuring the weight of the residue after the polylactic acid in the non-woven fabric of the present invention is dissolved by dichloromethane (more specifically, after the fiber portion of the non-woven fabric is dissolved).

The non-woven fabric of the present invention may be produced by an electrospinning method. Electrospinning is a well-known method for producing non-woven fabric. More specifically, electrospinning methods are performed by discharging a solution, which is obtained by dissolving a polymer (and, as necessary, a dispersion adjuvant) in a volatile solvent (for example, chloroform, dichloromethane, hexafluoroisopropyl alcohol, or a mixed solution thereof) into an electrostatic field formed between the electrodes, and forming threads of the solution toward the electrode (ground electrode), thereby producing a fiber-like substance. FIG. 1 shows a simple schematic view of an electrospinning method. The method shown in FIG. 1 is only an example of an electrospinning method, and any known electrospinning methods capable of producing the non-woven fabric of the present invention may be used for the production of the non-woven fabric of the present invention. FIG. 1 is briefly described below. By applying a high voltage to a polymer-dissolved solution in a syringe (having a nozzle on the top end), the polymer solution is discharged as a sharp conical drop. Further, by further increasing the voltage, the solution is ejected (sprayed) toward the ground electrode (for example, copper, aluminium, etc.), thereby forming a thin fiber (i.e., non-woven fabric) on the ground electrode. Therefore, in the method of FIG. 1, the ground electrode also serves as a collector.

In the present invention, the concentration of the biocompatible polymer in the biocompatible polymer-dissolved solution used for electrospinning method may be suitably determined; the concentration is generally about 1 to 30 mass %, preferably about 2 to 25 mass %, more preferably about 3 to 20 mass %.

Further, the distance between the electrodes (in FIG. 1, the distance between the syringe and the ground electrode) generally depends on the charging amount, the nozzle size, the liquid flow amount during spinning, the concentration of spinning liquid and the like, and may suitably be determined. For example, when the applied voltage is about 10 kV, the distance is preferably about 5 to 50 cm, more preferably about 10 to 30 cm. Further, the electrostatic potential to be applied is generally about 3 to 100 kV, preferably about 5 to 50 kV, further preferably about 5 to 30 kV.

In the production method of the non-woven fabric of the present invention, a bone prosthetic material is supplied during the production of non-woven fabric using an electrospinning method. More specifically, for example, the non-woven fabric of the present invention may be produced by spraying a small amount of a biocompatible polymer-dissolved solution using an electrospinning method to obtain a non-woven fabric, dispersing an appropriate amount of bone prosthetic material in the non-woven fabric, and further spraying the biocompatible polymer-dissolved solution thereto. The non-woven fabric of the present invention is preferably performed by repeating this series of steps several times to several tens of times (specifically, about 2 to 50 times, preferably about 5 to 10 times). In other words, the production process of the non-woven fabric of the present invention includes the above production procedure, and preferably includes several to several tens of times of the procedure. A preferable production process is a method of spraying the biocompatible polymer-dissolved solution at a rate of 0.5 to 1.5 µL/sec, and adding 0.1 to 0.2 g of a bone prosthetic material every 15 minutes. In this method, about 1 to 2 g of the bone prosthetic material is added in total.

Figure 2:
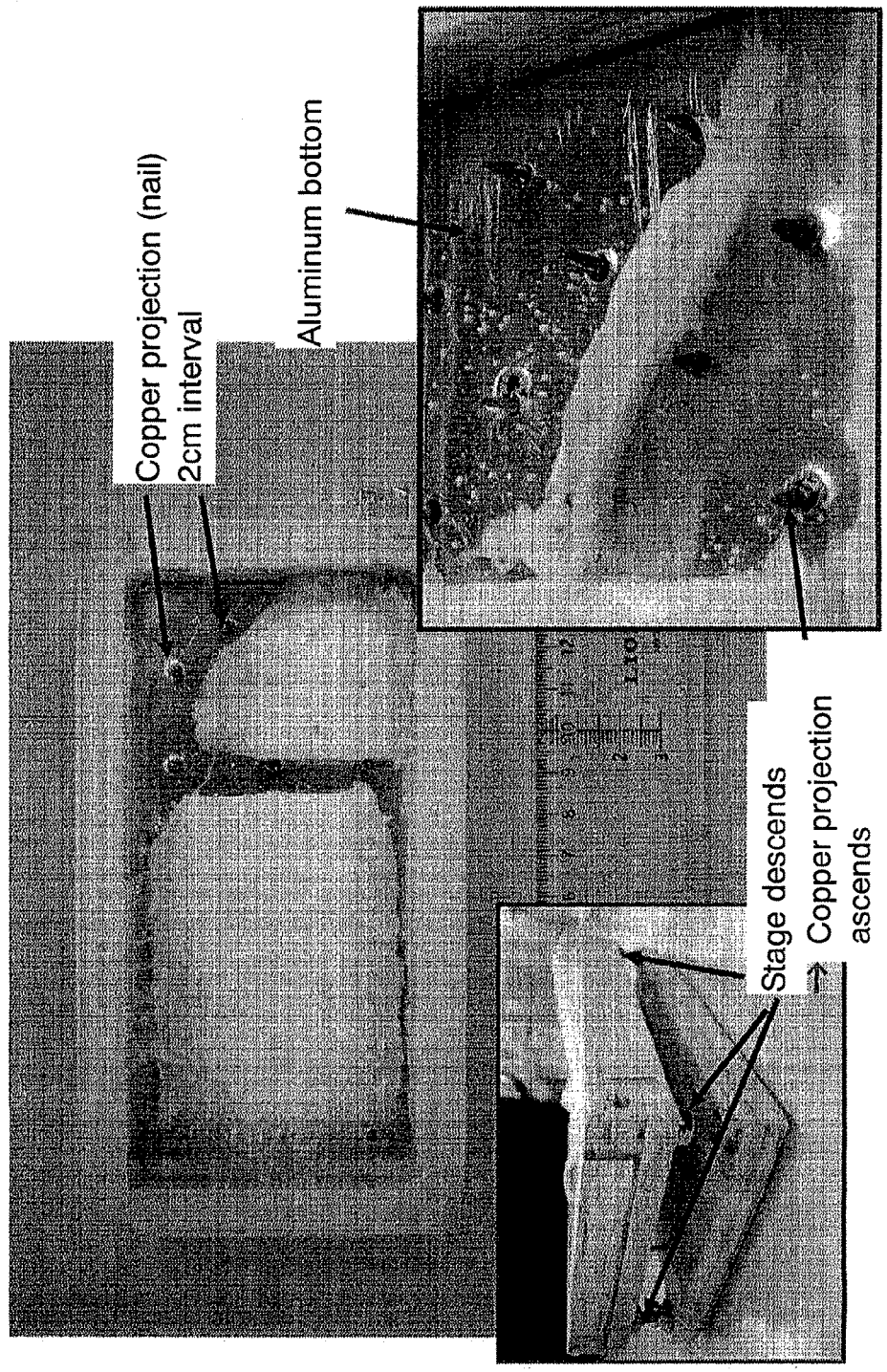
FIG. 2 Images showing an example of a ground electrode used for the production of the non-woven fabric of the present invention.

During the electrospinning method, when the produced non-woven fabric accumulates to a certain thickness, the negative charging of the ground electrode becomes difficult due to the accumulation of the non-woven fabric. This hinders the spraying of the biocompatible polymer-dissolved solution. For this reason, it has been difficult to produce a non-woven fabric with a relatively large thickness using a hitherto-known electrospinning method. Therefore, in the present invention, it is preferable to add, for example, the following structure to the ground electrode to enable production of a non-woven fabric having a relatively large thickness. The earth electrode is preferably not a simple metal plate (for example, an aluminum or copper plate), but provided with projections (preferably, cylindrical or conical projections) on the metal plate. Further, the projections are preferably movable up and down. By using such a ground electrode having the projections, when the thickness of the non-woven fabric increases and the negative charging of the ground electrode becomes difficult, it is possible to facilitate the negative charging of the electrode by moving the projections upward. The projections are preferably provided in the form of a grid with, for example, about 1 to 3 cm intervals therebetween. The sectional area of the projections is preferably about 0.001 to 0.5 cm$^2$, more preferably about 0.01 to 0.1 cm$^2$. The present invention also encompasses a ground electrode for electrospinning having such a structure. As described later, FIG. 2 shows an example of a ground electrode for electrospinning having the above structure.

Since the non-woven fabric of the present invention invariably ensures a significant increase in cell (in particular, osteoblast) proliferation efficiency (i.e., cell proliferation ability) when it is used as a cell culture scaffold, the non-woven fabric of the present invention may be suitably used as a cell culture scaffold, and also as a bone regeneration material. More specifically, in the case of bone damage due to external factors (for example, accident), or in the case of absorption or loss of bone due to internal factors (for example, osteoporosis, periodontal diseases), the non-woven fabric of the present invention enables quick bone regeneration (specifically, by being incorporated into or attached to the affected part). In particular, the non-woven fabric of the present invention has a desirable thickness, which was not possible for hitherto-known non-woven fabrics; therefore, the non-woven fabric of the present invention can be used to promote bone regeneration by, as in the hitherto-known non-woven fabrics, being embedded in the target part (affected part).

In particular, in the non-woven fabric of the present invention, the bone prosthetic material is entangled around the fibers of the non-woven fabric. With this structure, the bone prosthetic material has a high retention capability and appropriate toughness; therefore, the non-woven fabric of the present invention can be easily applied (embedded) to the affected part, even when the affected part has a complicated shape. The non-woven fabric also has superior cell permeability and liquid permeability.

A preferable application of the non-woven fabric of the present invention is, but not limited to, in particular, alveolar bone regeneration in the implant treatment.

In the hitherto-known GBR (Guided Bone Regeneration) method, it is necessary to first fill an alveolar bone regeneration region with a bone prosthetic material, and then apply a shield membrane to prevent infiltration of gingival tissue or epithelium tissue, which interferes with bone tissue regeneration, into the region (more specifically, the bone prosthetic material and the shield membrane must be sequentially applied and placed together). Therefore, the sequential procedure of filling the target region with a bone prosthetic material and then applying a shield membrane is burdensome for the user; further, this step requires a high level of skill from the user. In contrast, when the non-woven fabric of the present invention is used as a replacement of a bone prosthetic material, the non-woven fabric of the present invention and the shield membrane can be applied at the same time, thereby reducing the burden of the user with a simpler technique than the hitherto-known method. In particular, the hitherto-known methods often have a problem of leakage of bone prosthetic material from the applied part; however, the problem can be solved by using the non-woven fabric of the present invention instead of a bone prosthetic material. Further, since the non-woven fabric of the present invention is flexible, it can be deformed along the affected part, or cut into an appropriate shape according to the shape of the affected part.

Further, by extending the length from the bone prosthetic material included inside the non-woven fabric to the exterior of the non-woven fabric of the present invention (in other words, by increasing the thickness of the fiber layer (the fiber layer in contact with the gingival tissue or the epithelium tissue) of the non-woven fabric of the present invention), it is possible to suppress the infiltration of gingival tissue or epithelium tissue into the regeneration region (more specifically, it is possible to add a function as a shield membrane). In this case, the non-woven fabric of the present invention is used solely, instead of using the set of the shield membrane and the bone prosthetic material.

Further, as described above, the non-woven fabric of the present invention is produced using an electrospinning method by repeating a series of the steps of "spraying a small amount of a biocompatible polymer-dissolved solution to produce non-woven fabric, dispersing an appropriate amount of a bone prosthetic material on the non-woven fabric, and further spraying the biocompatible polymer-dissolved solution thereto." However, by slightly changing the production process, it is also possible to produce useful non-woven fabric of various forms. For example, by repeating a series of the steps of first spraying a large amount of a biocompatible polymer-dissolved solution to produce a wide and thick non-woven fabric, adding a bone prosthetic material only to a relatively narrow portion on the non-woven fabric, and spraying a biocompatible polymer-dissolved solution to the narrow portion, a top hat-shaped, non-woven fabric having a projected bone prosthetic material included in a part of the wide and thick non-woven fabric base can be obtained. If assuming that the non-woven fabric is a top hat, the wide and thick non-woven fabric is the brim, and the rest of the non-woven fabric containing a bone prosthetic material is the crown. This top hat-shaped, non-woven fabric is applied by embedding the crown portion in the alveolar bone regeneration region. In this manner, the brim portion serves to inhibit infiltration of gingival tissue or epithelium tissue into the region. More specifically, the top hat-shaped non-woven fabric serves both as a shield membrane and a bone prosthetic material.

As such, the non-woven fabric of the present invention may be used as a bone regeneration material. Further, the present invention also encompasses a structure in which osteoblasts or the like are adhered or added to the non-woven fabric of the present invention. More specifically, the present invention encompasses a bone regeneration material containing the non-woven fabric. The bone regeneration material may be made of only the non-woven fabric, or may also contain the above non-woven fabric containing osteoblasts. The incorporation of osteoblasts may be performed, for example, by a cell culture using the non-woven fabric as a scaffold material.

Further, the non-woven fabric of the present invention may be used as an osteoblast culture scaffold material. In this case, the non-woven fabric having the same feature as the above bone regeneration material may be used as an osteoblast culture scaffold material.

Furthermore, the non-woven fabric of the present invention is useful as a bone regeneration material. The bone regeneration material may be used for, for example, the following treatments, surgeries, or other usages.

Periodontal Tissue Regeneration and Oral Surgery Field

Guided tissue generation for infrabony defect, class II furcation lesion, shrinkage-type defect, and cleavage-type defect; guided bone generation for alveolar ridge bone augmentation, and bone generation in the vicinity of implant; alveolar ridge formation technique; sinus lift procedure for maxillary sinus bottom elevation technique; socket preservation method for extraction socket preservation; nasal cavity bottom elevation technique; bone extension surgery; bone filling after curettage of dead bone portion; bone filling after curettage of bone cancer tissue; bone regeneration in bone filling procedure for treating traumatic bone fracture; aesthetic treatments such as gingiva enlargement under bridge, root coating for gingival recession, reconstruction of interdental papilla, or other gingiva enlargement; and the like.

Orthopedic Field

Bone extension surgery; treatments after curettage of dead bone portion or after bone cancer tissue curettage, treatments of traumatic bone fracture, spinal compression fracture, bone reconstruction technique for nonunion treatment; bone extension surgery; medicinal ingredient carrier materials for osteoporosis treatment; and the like.

The present invention also encompasses a bone regeneration method that is performed by applying the non-woven fabric of the present invention to a target site subjected to bone (preferably alveolar bone) regeneration. The method can be used for, for example, the treatments or surgeries listed above.

Examples

The present invention is more specifically explained below. However, the present invention is not limited to these examples. In the experiments, the textbooks, etc. (for example, Molecular Cloning: A Laboratory Manual (3 Vol. Set); Cold Spring Harbor Laboratory Press), listed in the technical field section may suitably be referred to.

Production of Non-Woven Fabric 1

43 g of a mixed solution of hexafluoroisopropyl alcohol: dichloromethane=8:2 (mass ratio) was added to 7 g of a polylactic acid (Mitsui Chemicals, Inc. LACEA, H-400), thereby obtaining a polylactic acid solution (14 w/w %). A syringe (Henke SASS WOLF, 5 mL) was filled with the obtained polylactic acid solution, combined with a needle (non-bevel needle 21G1.1/2, Terumo Corporation), and set on an electrospinning device. The distance from the syringe to the ground (the target) was set to 8 cm and the polylactic acid solution was sprayed by 10 kV voltage application, by changing conditions, i.e., by varying the spraying duration and spraying amount, as shown in Table 1. During the spray, a bone prosthetic material (OSFERION, Olympus Terumo Biomaterials Corporation) was added every 15 minutes as evenly as possible until the total addition amount became 2 g. A bone prosthetic material (OSFERION) having a diameter of 0.5 to 1.5 mm (standard value) was used. After the total amount of the bone prosthetic material was added, the polylactic acid solution was sprayed for another 15 minutes. In this manner, the four types of nonwoven fabric shown in Table 1 were produced.

In this production method, an aluminum plate provided with copper projections movable up and down was used as a ground electrode (also serving as a collector). FIG. 2 shows a schematic view of the ground electrode. During the above spraying step, the copper projections were raised by 0.5 mm every 15 minutes.

TABLE 1

Samples produced by electrospinning

| Produced Non-woven fabrics | Spray Amount | Spray Duration | Amount of addition of bone prosthetic material | Interval of addition of bone prosthetic material | Total addition amount of bone prosthetic material |
|---|---|---|---|---|---|
| Non-woven fabric without bone prosthetic material (Sample 0) | 0.6 µL/sec | 120 min | — | — | — |
| Non-woven fabric (Sample 1) | 0.6 µL/sec | 165 min | 0.2 g | 15 min | 2 g |
| Non-woven fabric (Sample 2) | 1.2 µL/sec | 165 min | 0.2 g | 15 min | 2 g |
| Non-woven fabric (Sample 3) | 1.2 µL/sec | 315 min | 0.1 g | 15 min | 2 g |

Evaluation of Physical Properties of Non-Woven Fabric 1

Using the method below, thickness, bulk density, and proportion of bone prosthetic material with respect to the four types of non-woven fabric (Samples 0, 1, 2, and 3); and the fiber diameter of the fibers of each fabric were measured.

Each sample was cut into a rectangle (about 4 cm$^2$), and the weight of each rectangle was measured. The length, width, and thickness of the sample were found using a thickness gauge (Digital thickness gauge, Ozaki Seisakusho, DG-205M). The obtained values of length, width, and thickness were multiplied to find the bulk (cm$^3$). The thickness was found by averaging the measurement values of 20 portions.

The bulk density was determined according to the following formula from the weight and the bulk of each sample.

Bulk density (g/cm$^3$)=sample weight (g)/sample bulk (cm$^3$)

Each sample thus cut into a rectangle was placed in a conical tube, and 50 mL of dichloromethane was added thereto, thereby dissolving the polylactic acid contained in the sample. Then, leaving a precipitate in the conical tube, the supernatant was removed. The dichloromethane in the precipitate was evaporated, and the weight of the remaining precipitate was measured as a weight of the bone prosthetic material. The proportion of bone prosthetic material was determined according to the following formula.

Proportion of bone prosthetic material (%)=(dichloromethane insolubles(precipitates)/sample weight)×100

Further, an image of the cross section of each sample was obtained using a scanning electron microscope (Hitachi High-Technologies Corporation, S-3400N). From a 500× magnified image obtained by the scanning electron microscope, the fiber diameter was found using IMAGEJ (Ver.

1.43u; image processing software developed by NIH). The fiber diameter of each sample was found by averaging the diameters of 50 fibers.

Figure 3:
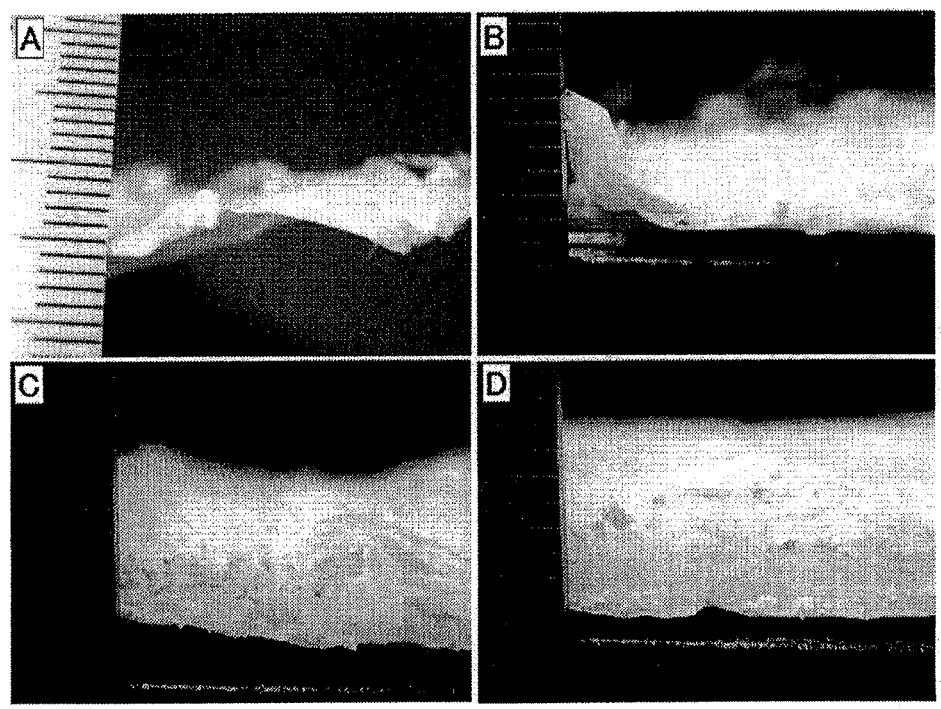
FIG. 3 Cross-sectional views showing the non-woven fabric of the present invention (and a general non-woven fabric produced by an electrospinning method).

FIG. 3 shows images of cross sections of the samples. In FIG. 3, Images A, B, C, and D correspond to Samples 0, 1, 2, and 3, respectively. By referring to FIG. 3, it was confirmed that, unlike Sample 0, Samples 1 to 3 containing a bone prosthetic material had a sufficient thickness. FIG. 4 shows images of the cross section of Sample 3 obtained by a scanning electron microscope. FIG. 4 also shows a schematic view thereof.

Table 2 shows the evaluation results of the physical properties.

TABLE 2

Evaluation of physical properties of non-woven fabrics

| Samples | Proportion of bone prosthetic material | Thickness | Fiber Diameter | Bulk Density |
|---|---|---|---|---|
| Non-woven fabric without bone prosthetic material (Sample 0) | 0% | 0.163 mm ± 0.044 | 2.685 µm ± 0.322 | — |
| Non-woven fabric (Sample 1) | 97.4% | 2.415 mm ± 0.430 | 3.435 µm ± 0.741 | 0.179 g/cm$^3$ |
| Non-woven fabric (Sample 2) | 91.6% | 2.733 mm ± 0.427 | 3.170 µm ± 0.997 | 0.194 g/cm$^3$ |
| Non-woven fabric (Sample 3) | 89.0% | 2.500 mm ± 0.529 | 2.630 µm ± 0.473 | 0.216 g/cm$^3$ |

Furthermore, for Samples 1 to 3, the porosity (%) of the non-woven fabric and the porosity (%) of the fibers of the non-woven fabric were calculated. In the calculation, a true density of 1.26 g/cm$^3$ was used as the true density of the polylactic acid, and a true density of 3.17 g/cm$^3$ was used as the true density of the bone prosthetic material (OSFERION). The true densities were found using a dry automatic densometer (ACCUPYC1330; Shimadzu Corporation).

recovered when released. Such non-woven fabrics are suitable as a bone regeneration material.

Evaluation of Cell Proliferation Ability of Non-Woven Fabric

The cell proliferation abilities of the non-woven fabrics (Samples 1 to 3) were examined according to the following procedure. More specifically, the DNA amount of the cells proliferated by each sample was examined to determine cell proliferation ability.

Cell Culture

Each non-woven fabric sample (Samples 1 to 3) was cut into a piece having the same size as the bottom of a 48-well plate (Sumitomo Bakelite Co., Ltd., SUMILON, MS-80480), and placed on the bottom of the well. Each sample contained about a 50 mg-equivalent of bone prosthetic material. As a control sample, about 50 mg of a bone prosthetic material (OSFERION) itself was placed on the bottom of a well of the 48-well plate.

A stainless steel tube (penicillin cup) was placed on each evaluation sample, and 500 µL of 10% FBS/MEM culture medium (10% FBS/MEM culture medium containing antibiotics and glutamic acid; hereinafter, "10% FBS/MEM culture medium" denotes this medium) was added thereto. Each sample thus prepared was centrifuged for 5 minutes using a plate centrifuge (2500 rpm, room temperature). After evacuation, the samples were further centrifuged for another 5 minutes (2500 rpm, room temperature). Further, 200 µL of 10% FBS/MEM culture medium was added thereto, and the samples were incubated for at least an hour in an incubator (37° C., 5% CO$_2$). 500 µL of the culture medium was removed by sucking. Human osteosarcoma-derived cells MG-63 were suspended in a 10% FBS/MEM culture medium in an amount of 1.6×10$^5$ cells/mL, and 100 µL each of the resulting cells was seeded in each well (1.6×10$^4$ cells/well). After 5 hours incubation, the cells were attached to the evaluation samples. Thereafter, 200 µL of 10% FBS/MEM culture medium was added thereto, and the samples were cultured. The samples at Day 1, Day 3, and Day 8 of the incubation were examined for cell proliferation ability.

Measurement of Cell Proliferation Ability

After the culture, each evaluation sample (non-woven fabric) having cells attached thereto was taken out and placed in a plate containing PBS (phosphate buffer physi-

TABLE 3

| | Per 1 cm$^3$ of non-woven fabric | | | | | | | |
|---|---|---|---|---|---|---|---|---|
| Item | (a) Proportion of bone prosthetic material (OSFERION) | (b) Bulk Density (g/cm$^3$) | (c) Weight of bone prosthetic material (g) | (d) Bulk corresponding to bone prosthetic material (cm$^3$) | (e) Weight of polylactic acid (g) | (f) Bulk corresponding to polylactic acid (cm$^3$) | (g) Total bulk of bone prosthetic material and polylactic acid (cm$^3$) | (h) Void ratio of Non-woven fabric (%) | (i) Void ratio of fibers of Non-woven fabric (%) |
| Sample 1 | 97.4% | 0.179 | 0.174 | 0.055 | 0.005 | 0.004 | 0.059 | 94.1% | 99.6% |
| Sample 2 | 91.6% | 0.194 | 0.178 | 0.056 | 0.016 | 0.013 | 0.069 | 93.1% | 98.6% |
| Sample 3 | 89.0% | 0.216 | 0.192 | 0.061 | 0.024 | 0.019 | 0.080 | 92.0% | 98.0% |
| Calculation formula | | | (a × b) | (c/3.17) | (b − c) | (e/1.26) | (d + f) | (1 − g) × 100 | [1 − {f/(1 − d)}] × 100 |

The thickness of the polylactic acid non-woven fabric (Sample 0) that does not contain a bone prosthetic material was small, namely, 0.163 mm; this thickness is not sufficient, in particular, as a bone regeneration material serving as a filler of the affected part (bone defect portion). The polylactic acid non-woven fabrics (Samples 1 to 3) containing a bone prosthetic material were all relatively thick non-woven fabrics having a thickness of 2 to 3 mm; therefore, when the non-woven fabrics were pressed by hand, the thickness was ological saline solution). The weight of each evaluation sample containing PBS was measured, and a water absorption amount of the evaluation sample was found from the dry weight of the evaluation sample and the weight of the evaluation sample containing PBS (by subtracting the dry weight (measured at the time when each evaluation sample was cut into a piece of the same size as the bottom of the plate) before being subjected to the experiment from the weight of the evaluation sample containing PBS).

A TE buffer solution (Tris/Tris-HCl 10 mM, EDTA 1 mM) was added to the plate so that the total solution amount of the sample including the water absorption amount and the TE buffer solution became 1200 µL. A sequential freezing and thawing of the sample (frozen at −80° C. and dissolved at room temperature) were conducted twice, followed by ultrasonic treatment for 30 minutes, thereby disrupting the cells. 100 µL of a cell lysate liquid (i.e., disrupted cell liquid obtained through the freezing and thawing, and ultrasonic treatment) was added to a 96-well fluorescence measurement plate (Nunc black microwell, cat. 137101) to obtain measurement samples.

Figure 5:
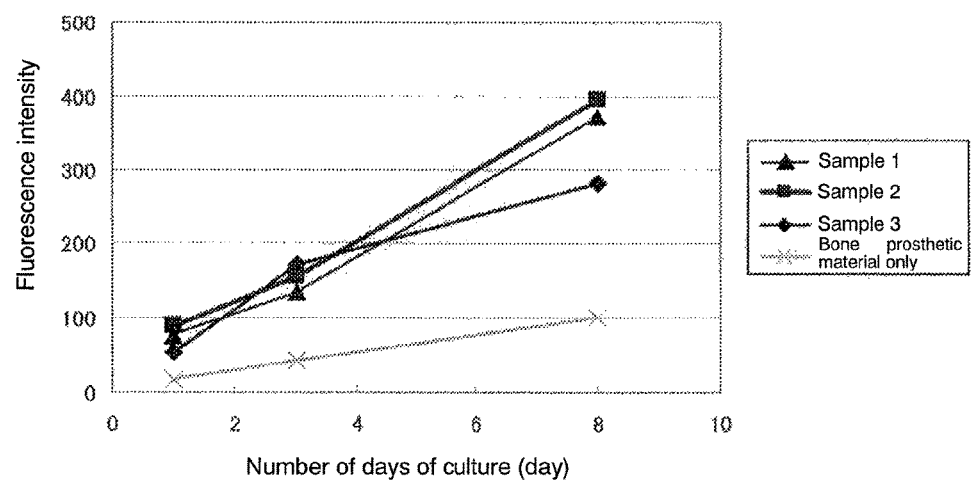
FIG. 5 A graph showing the cell proliferation abilities of Samples 1 to 3 of the non-woven fabric of the present invention.
Figure 6A:
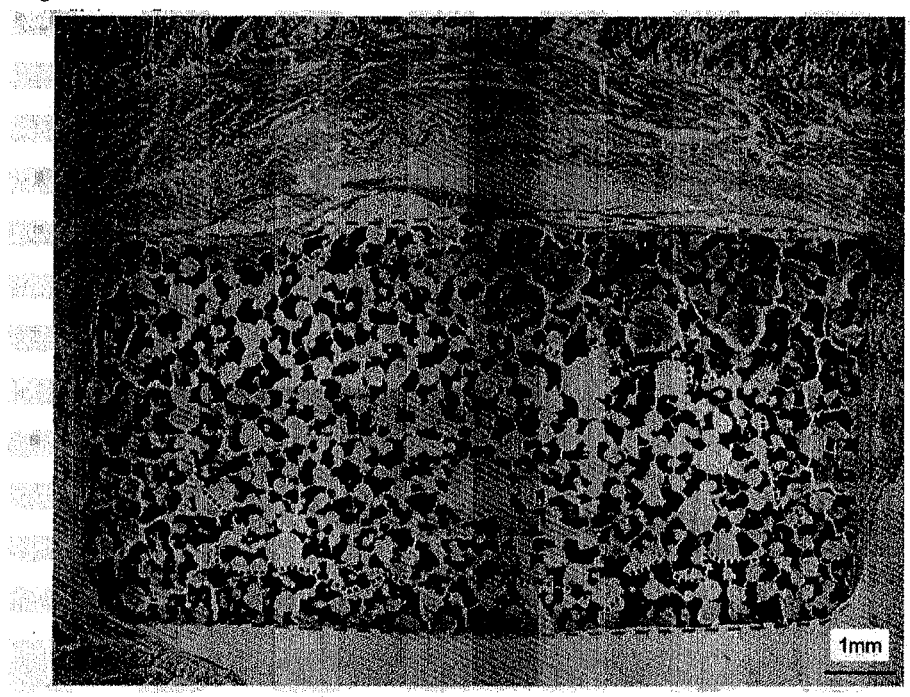
FIG. 6a An image of a tissue fragment for showing the infiltration level of a connective tissue into a block-shaped bone prosthetic material when the block-shaped bone prosthetic material (OSFERION block) is implanted into a rat. The outer broken line shows the outline of the implanted bone prosthetic material, and the inner dotted line shows the top end of the tissue infiltrated into the bone prosthetic material.
Figure 6B:
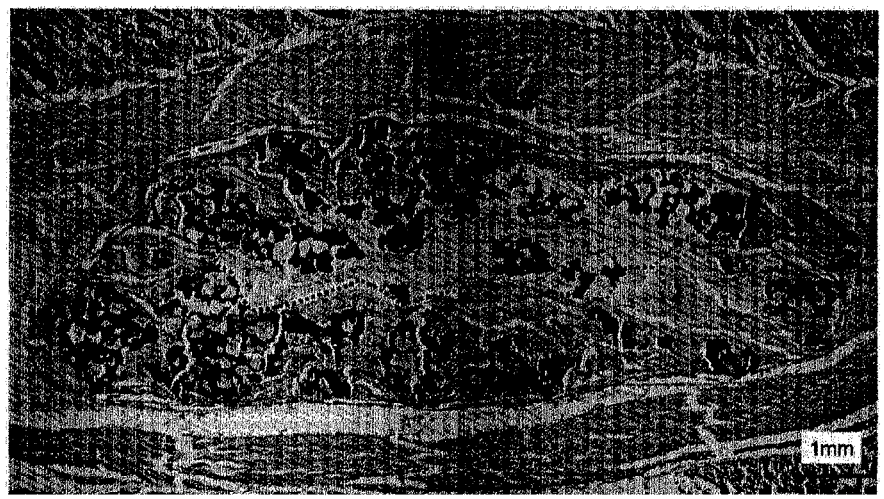
FIG. 6b An image of a tissue fragment for showing the infiltration level of a connective tissue into a non-woven fabric when the non-woven fabric of the present invention is implanted into a rat. The outer broken line shows the outline of the implanted non-woven fabric, and the inner dotted line shows the top end of the tissue infiltrated into the non-woven fabric.

PICOGREEN (Invitrogen) was diluted (from 100 µL to 20 mL) with a TE buffer solution; 100 µL thereof was added to each measurement sample, and the mixture was incubated for 5 minutes at room temperature. The fluorescence intensity of each sample was measured using a fluorescence plate reader (SpectraMax GEMINI XPS, Molecular Devices) at an excitation wavelength of 480 nm and an emission wavelength of 520 nm. PICOGREEN is a colorant specifically used for double-strand DNA; therefore, the resulting fluorescence intensity reflects the DNA amount (and number of the cells). FIG. 5 shows the results. In comparison with the case (control) using only a bone prosthetic material, many cells were adhered to the thick polylactic acid non-woven fabrics (Samples 1 to 3) containing a bone prosthetic material. The cell proliferation was thus confirmed. Therefore, it was confirmed that these non-woven fabrics are superior as a bone regeneration material.

Measurement of Pore Size of Non-Woven Fabric

The pore size (mode) of the non-woven fabric was measured according to the half-dry method (ASTM E1294-89) using perfluoro polyester (using a circular measurement adopter having a diameter of 7 mm). A capillary flow porometer (CFP-1200-AEL, Porous Materials Inc.) was used as the measurement device. The class interval in the calculation of the mode was 1 µm.

Production of Non-Woven Fabric 2

45 g of a mixed solution of hexafluoroisopropyl alcohol:dichloromethane=8:2 (mass ratio) was added to 5 g of a polylactic acid (Evonik Degussa Japan, RESOMER®) to dissolve the polylactic acid, thereby obtaining a polylactic acid solution (10 wt %) A syringe (Henke SASS WOLF, 5 mL) was filled with the obtained polylactic acid solution, and set on an electrospinning device (MEC Co., Ltd., NF-103A). The distance from the syringe to the ground electrode (the target: a 4×4 cm aluminum block having the same mechanism as that in FIG. 2) was set to 22 cm, and the polylactic acid solution was sprayed by 15 kV voltage application for 90 minutes in total in an amount of 1 ml/hour. During the spray, 0.033 g of a bone prosthetic material (OSFERION G1, Olympus Terumo Biomaterials Corporation) and powder obtained by pulverizing the bone prosthetic material and adjusting the particle diameter by sieving were evenly added 30 times every 3 minutes until the total addition amount became about 1 g. In this manner, the five types (A, B, C, D, and E) of non-woven fabric shown in Table 4 were produced.

A non-woven fabric was produced in the same manner as above using a block-shaped (a 20 mm×10 mm×3.5 mm rectangular solid) OSFERION (OSFERION A1) as a bone prosthetic material. This non-woven fabric is hereinafter referred to as "non-woven fabric F (Table 4).

TABLE 4

| Produced Non-woven fabrics | Spray Amount (mL/hour) | Spray Duration (min) | Amount of per addition of bone prosthetic material (g) | Interval of addition of bone prosthetic material (min) | Total addition amount of bone prosthetic material (g) | Particle diameter of bone prosthetic material (µm) |
|---|---|---|---|---|---|---|
| Non-woven fabric without bone prosthetic material (Non-woven fabric A) | 1.0 | 90 | — | — | — | — |
| Non-woven fabric B | | 93 | 0.033 | 3 | 1 | 75-180 |
| Non-woven fabric C | | | | | | 150-810 |
| Non-woven fabric D | | | | | | 500-1500 |
| Non-woven fabric E | | | 0.067 | 5.8 | | 4700-8000 |
| Non-woven fabric F | 1.0 | 93 | 0.5 | 31 | 1 | 20 mm × 10 mm × 3.5 mm block |

Evaluation of Physical Properties of Non-Woven Fabric 2

Using the method below, thickness, bulk density, and proportion of bone prosthetic material with respect to the six types of non-woven fabric (A to F), and the fiber diameter of the fibers of each fabric were measured and calculated.

Each sample was cut into a 4×4 cm square, and the weight of each sample was measured. The thickness of the sample was measured using a DIGIMATIC micrometer (Mitutoyo Corporation, CLM1-15QM). The thickness of the sample was found by averaging the measurement values of 20 portions.

Then, in the same manner as the method explained in the above section "Evaluation of physical properties of non-woven fabric 1," bulk density, proportion of bone prosthetic material of Non-woven fabrics A to F, and the fiber diameter of the fibers of each fabric were measured and calculated, except that the fiber diameter was found using a 2000× magnified electron-microscopic image, instead of using a 500× magnified image.

Table 5 shows the results of evaluation of physical properties. Since Non-woven fabric F was produced using a block-shaped bone prosthetic material, the bulk density of Non-woven fabric F was greater than those of other non-woven fabrics.

TABLE 5

| Samples | Proportion of bone prosthetic material (%) | Thickness (mm) | Fiber Diameter (μm) | Bulk Density (g/cm³) |
|---|---|---|---|---|
| Non-woven fabric without bone prosthetic material (Non-woven fabric A) | 0 | 0.24 ± 0.02 | 2.52 ± 0.20 | 0.273 |
| Non-woven fabric B | 75.0 | 1.70 ± 0.18 | 1.99 ± 0.26 | 0.379 |
| Non-woven fabric C | 92.43 | 2.96 ± 0.17 | 2.43 ± 0.23 | 0.214 |
| Non-woven fabric D | 94.0 | 3.59 ± 0.39 | 2.20 ± 0.33 | 0.152 |
| Non-woven fabric E | 92.1 | 4.68 ± 1.09 | 2.08 ± 0.15 | 0.145 |
| Non-woven fabric F | 90.9 | 1.16 ± 1.34 | 2.25 ± 0.31 | 0.595 |

Furthermore, the porosity (%) of each non-woven fabric and the porosity (%) of the fibers of each non-woven fabric were calculated. More specifically, the calculation was performed using a true density of 1.26 g/cm³ as the true density of the polylactic acid, and a true density of 3.17 g/cm³ as the true density of the bone prosthetic material (OSFERION) in the same manner as the method explained in the above section "Evaluation of physical properties of non-woven fabric 1," except that the porosity of the fibers of Non-woven fabric F was calculated using a true density of 0.7065 g/cm³ as the true density of the bone prosthetic material, because the block-shaped bone prosthetic material contained in Non-woven fabric F has many voids. Table 6 shows the results.

The porosity of the fibers of Non-woven fabric F was lower than those of the other non-woven fabrics, as it contains a block-shaped bone prosthetic material. Therefore, Non-woven fabric F was relatively harder than the other non-woven fabrics.

TABLE 6

| Samples | Void ratio of Non-woven fabric (%) | Void ratio of fibers of Non-woven fabric (%) |
|---|---|---|
| Non-woven fabric without bone prosthetic material (Non-woven fabric A) | 78.3 | 78.3 |
| Non-woven fabric B | 83.5 | 91.7 |
| Non-woven fabric C | 92.5 | 98.6 |
| Non-woven fabric D | 94.8 | 99.2 |
| Non-woven fabric E | 94.9 | 99.1 |
| Non-woven fabric F | 78.6 | 81.6 |

Production of Non-Woven Fabric 3

Non-woven fabric α was produced in the same manner as in the method explained in the above section "Production of non-woven fabric 2," except that the concentration of the polylactic acid solution was 5 wt % and that the polylactic acid solution was sprayed from the electrospinning device for 195 minutes in total in an amount of 1 ml/hour; after the polylactic acid solution was sprayed for 15 minutes, 0.03 g of a bone prosthetic material was added every 6 minutes until the total addition amount became about 1 g.

Evaluation of Physical Properties of Non-Woven Fabric 3

In the same manner as the method explained in the above section "Evaluation of physical properties of non-woven fabric 2," the thickness, bulk density, and proportion of bone prosthetic material of Non-woven fabric α, and the fiber diameter of the fibers of the three-dimensional fabric were measured and calculated. Further, the porosity (%) of the three-dimensional non-woven fabric and the porosity (%) of the fibers of the three-dimensional non-woven fabric were calculated. Tables 7 and 8 show the results.

TABLE 7

| Sample | Proportion of bone prosthetic material (%) | Thickness (mm) | Fiber Diameter (μm) | Bulk Density (g/cm³) |
|---|---|---|---|---|
| Non-woven fabric α | 95.0 | 3.91 | 0.35 ± 0.17 | 0.156 |

TABLE 8

| Sample | Void ratio of Non-woven fabric (%) | Void ratio of fibers of Non-woven fabric (%) |
|---|---|---|
| Non-woven fabric α | 94.7 | 99.3 |

Production of Non-Woven Fabric 4

Using a 6×25 cm aluminum block as a ground electrode, Non-woven fabric β was produced in the same manner as the method explained in the above section "Production of non-woven fabric 2," except that the interval was 16 cm, and that the polylactic acid solution was sprayed for 360 minutes in total in an amount of 1 ml/hour; during the spray, 0.135 g of a bone prosthetic material (OSFERION) was evenly added to a 4×16 cm sample 59 times every 6 minutes until the total addition amount became about 8 g.

Evaluation of Physical Properties of Non-Woven Fabric 4

In the same manner as the method explained in the above section "Evaluation of physical properties of non-woven fabric 2," the thickness, bulk density, and proportion of bone prosthetic material of Non-woven fabric 3, and the fiber diameter of the fibers of the three-dimensional fabric were measured and calculated. Further, the porosity (%) of the three-dimensional non-woven fabric and the porosity (%) of the fibers of the three-dimensional non-woven fabric were calculated. Tables 9 and 10 show the results.

TABLE 9

| Sample | Proportion of bone prosthetic material (%) | Thickness (mm) | Fiber Diameter (μm) | Bulk Density (g/cm³) |
|---|---|---|---|---|
| Non-woven fabric β | 89.0 ± 1.1 | 6.34 ± 0.18 | 2.11 ± 0.24 | 0.155 |

TABLE 10

| Sample | Void ratio of Non-woven fabric (%) | Void ratio of fibers of Non-woven fabric (%) |
| --- | --- | --- |
| Non-woven fabric β | 94.3 | 98.6 |

Implant of non-woven fabric

Non-woven fabric β was implanted into a rat, and the level of cell infiltration into the connective tissue was examined. As a control, the block-shaped bone prosthetic material itself (OSFERION A1) was also implanted to a rat.

A male SD rat (8 weeks old, about 200 g) was purchased to be used as an experiment animal. The rat was anesthetized by inhalation of 2.5% isoflurane, the back hair was shaved to expose the target site, and the site was sterilized with ISODINE® and a rubbing alcohol. The skin of the back was cut open, and a gap was made in the loose connective tissue. Non-woven fabric β or a block-shaped bone prosthetic material (10×10×5 mm, Olympus Terumo Biomaterials Corporation, cut out from OSFERION A1) was embedded in the gap, and the incision was closed with a suture. Two weeks after the implant, the rat subjected to the implant was bled from the abdominal aorta under anesthesia by inhalation of 2.5% isoflurane so that the rat was euthanized. After confirming of the death of the rat, the embedded specimen with the surrounding tissue was obtained. The obtained sample was immersed in a 10% neutral buffered formalin liquid (MILDFORM®, Wako Pure Chemical Industries, Ltd.), and immobilized. Thereafter, a frozen undecalcified tissue fragment was obtained from the sample to be subjected to hematoxylin-eosin staining. The resulting tissue fragment sample was observed with an optical microscope. Tables 6a and 6b show the results. The infiltration of the Non-woven fabric β into the connective tissue was more desirable than that of the block-shaped bone prosthetic material.

Examination of Cell Infiltration Property 1

Cell Culture

Each of Non-woven fabrics A to D was cut into a piece having a diameter of about 1 cm, and placed on the bottom of a 24-well plate (Sumitomo Bakelite Co., Ltd., SUMILON, MS-80480). Each evaluation sample was pressed with a penicillin cup (stainless steel tube), and wet with 10000 µL of a 10% FBS/MEM culture medium containing antibiotics and glutamic acid (hereinafter, all 10% FBS/MEM culture mediums contain antibiotics and glutamic acid unless otherwise specified), followed by evacuation. The samples were incubated in an incubator for at least an hour at 37° C., 5% $CO_2$. Previously cultured MG-63 (derived from human osteosarcoma, Human Science Research Resources Bank, Lot. 05262004) was suspended in a 10% FBS/MEM culture medium in an amount of $3.2×10^5$ cells/mL, and 100 µL thereof was seeded in each well ($3.2×10^4$ cells/well). After overnight culture, the cells were used as evaluation samples.

Evaluation of Cell Infiltration Property

The cells were immobilized with a 4% paraformaldehyde solution for an hour, and washed with PBS. Thereafter, each sample was frozen with hexane under dry ice-cooling, and embedded in 4% CMC in the frozen state. The frozen sample was sliced into a 30 µL thick piece, and subjected to hematoxylin-eosin staining (HE staining). The sliced sample was observed with an upright microscope (Olympus Corporation, BH-2). Further, using IMAGEJ Ver 1.44, the maximum cell infiltration distance was measured. FIG. 7 shows the results. It was confirmed that the cell infiltration property increases as the porosity of the fabric and the porosity of the fibers increase.

Production of Non-Woven Fabric 5

Non-woven fabric γ was produced in the same manner as the method explained in the above section "Production of non-woven fabric 4," except that the polylactic acid solution was sprayed for 120 minutes in total; during the spray, 0.135 g of a bone prosthetic material (OSFERION G1) was evenly added to a 4×16 cm sample 39 times every 3 minutes until the total addition amount became about 5.3 g.

Examination of Cell Infiltration Property 2

The cell infiltration properties of Non-woven fabric β and Non-woven fabric γ were examined as follows by performing cell culture using Non-woven fabrics β and γ. Each of Non-woven fabrics β and γ was cut into a piece having a diameter of about 1 cm. Each sample was completely wet in a 10% FBS/MEM culture medium by evacuation. Then, the samples were incubated in an incubator for at least an hour at 37° C., 5% $CO_2$. Previously cultured MG-63 (derived from human osteosarcoma, Human Science Research Resources Bank, Lot. 05262004) was suspended in a 10% FBS/MEM culture medium in an amount of $1.6×10^5$ cells/mL, and each evaluation sample was immersed in 10 mL of the cell solution for 60 minutes. Each sample was gently stirred in the solution every 15 minutes. Each sample was taken out from the cell solution, and placed on the bottom of a 24-well plate (Sumitomo Bakelite Co., Ltd., SUMILON, MS-80240). 1 mL of medium was added, and each sample was pressed with a penicillin cup (stainless steel tube) and cultured overnight. The obtained cell-culture non-woven fabrics were used as samples. The cells were immobilized with a 4% paraformaldehyde solution for an hour, and washed with PBS. Thereafter, the sample was frozen with hexane under dry ice-cooling, and embedded in 4% CMC in the frozen state. The frozen sample was sliced into a 30 µL-thick piece, and subjected to HE staining. The sliced sample was observed with a microscope (Olympus Corporation, BH-2) to evaluate the cell infiltration property.

In the same manner as the method explained in the above section "Measurement of pore size of non-woven fabric," the pore size of each non-woven fabric was measured. However, in the measurement of the pore sizes of Non-woven fabrics β and γ, the outer surfaces of the non-woven fabrics were peeled off, and the obtained layer was used for the measurement.

FIG. 8 shows the results. The pore sizes in FIG. 8 are the modes.

Figure 9:
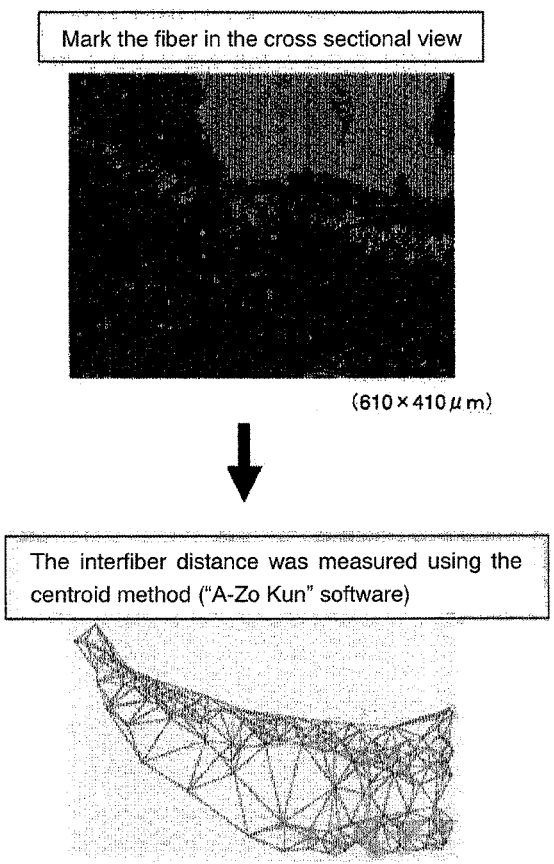
FIG. 9 Drawings schematically showing a measurement method for a distance between fibers (an interfiber distance).

Furthermore, the interfiber distance of the non-woven fabric was measured in the following manner. Each measurement sample (non-woven fabric) was immersed in PBS, and defoamed under reduced pressure. The sample wet with PBS was sunk in 4% CMC (carboxy methyl cellulose) gel and frozen, thereby preparing a frozen block. A sample having a thickness of 2 µm was made from the obtained block, and sealed in a resin between a slide glass and a cover glass. A sliced sample was observed with a phase contrast microscope. The cross section of the fiber was detected from the obtained image, and the interfiber distance was measured using the centroid method. The analysis in the centroid method was performed using "A-Zo Kun" software (Asahi Kasei Engineering Corporation, Ver. 2.20). FIG. 9 shows the summary of the analysis. The interfiber distances of Non-woven fabrics β and γ, and Non-woven fabric sample 2 thus measured were 18.4 µm, 27.2 µm, and 33.3 µm, respectively.

Examination of Cell Infiltration Property 3 (Reference Example)

In order to analyze the relation between the cell infiltration property and the pore size of the non-woven fabric, a general non-woven fabric (flat non-woven fabrics (i) to (iii): Table 11) was produced, and the cell infiltration property was examined.

TABLE 11

| Produced Non-woven fabrics | Spray Amount (mL/hour) | Spray Duration (min) |
|---|---|---|
| Non-woven fabric (i) | 1.0 | 60 |
| Non-woven fabric (ii) | | 180 |
| Non-woven fabric (iii) | | |

More specifically, 5 g of a mixed solution of hexafluoroisopropyl alcohol:dichloromethane=8:2 (mass ratio) was added to 5 g of a polylactic acid (Evonik Degussa Japan, RESOMER®, L 206S) to dissolve the polylactic acid, thereby obtaining a polylactic acid solution (10 wt %). A syringe (Henke-Sass, Wolf GmbH, 5 mL) was filled with the obtained polylactic acid solution, and set on an electrospinning device (MEC Co., Ltd., NF-103A). The distance from the syringe to the ground electrode (the target: 3×3 cm aluminum block) was set to 25 cm and the polylactic acid solution was sprayed by 15 kV voltage application for 60 minutes in total in an amount of 1 ml/hour, thereby obtaining Non-woven fabric (i). Further, Non-woven fabrics (ii) and (iii) were obtained in the same manner as Non-woven fabric (i), except that a different type of rotating drum was used as the ground electrode.

The cell infiltration properties of Non-woven fabrics (i) to (iii) were examined in the same manner as in the above section "Examination of cell infiltration property 2." However, in the pore size measurement of Non-woven fabric (i), the class interval in the calculation of the mode was 0.1 μm. FIG. 10 shows the results. The pore sizes in FIG. 10 are the modes. The "maximum infiltration distance" in FIG. 10 was found from images of HE-stained tissue fragments. The interfiber distances of Non-woven fabrics (i), (ii), and (iii) thus measured were 7.3 μm, 13.4 μm, and 15.8 μm, respectively.

The invention claimed is:

1. A non-woven fabric containing a bone prosthetic material wherein the bone prosthetic material is not incorporated in a single fiber, but present between biocompatible fibers that constitute the non-woven fabric, wherein the bone prosthetic material has a particle diameter of about 50 to 5000 μm, the fibers of the non-woven fabric have a porosity of 80 to 99.99%, and the biocompatible fibers have an average fiber diameter of about 0.05 to 20 μm.

2. The non-woven fabric according to claim 1, wherein the biocompatible fibers contain a biocompatible polymer.

3. The non-woven fabric according to claim 2, wherein the biocompatible polymer is at least one member selected from the group consisting of polylactic acid, polyglycolic acid, polylactic acid-polyglycolic acid copolymer, polycaprolactone, chitin, collagen, polylysine, polyarginine, hyaluronic acid, sericin, cellulose, dextran, and pullulan.

4. The non-woven fabric according to claim 1, wherein the bone prosthetic material is at least one member selected from the group consisting of β-tricalcium phosphate, α-tricalcium phosphate, hydroxyapatite, dibasic calcium phosphate dehydrate, octacalcium phosphate, tetracalcium phosphate, alumina, zirconia, calcium aluminate ($CaO$—$Al_2O_3$), aluminosilicate ($Na_2O$—$Al_2O_3$—$SiO_2$), bioactive glass, quartz, and calcium carbonate.

5. The non-woven fabric according to claim 1, wherein the non-woven fabric has a porosity of 78.5 to 97%.

6. The non-woven fabric according to claim 1, wherein the bulk density (g/cm³) of the non-woven fabric is 0.1 to 0.6.

7. A bone regeneration material comprising the non-woven fabric according to claim 1.

8. An osteoblast culture scaffold material comprising the non-woven fabric according to claim 1.

* * * * *